Figure 1:
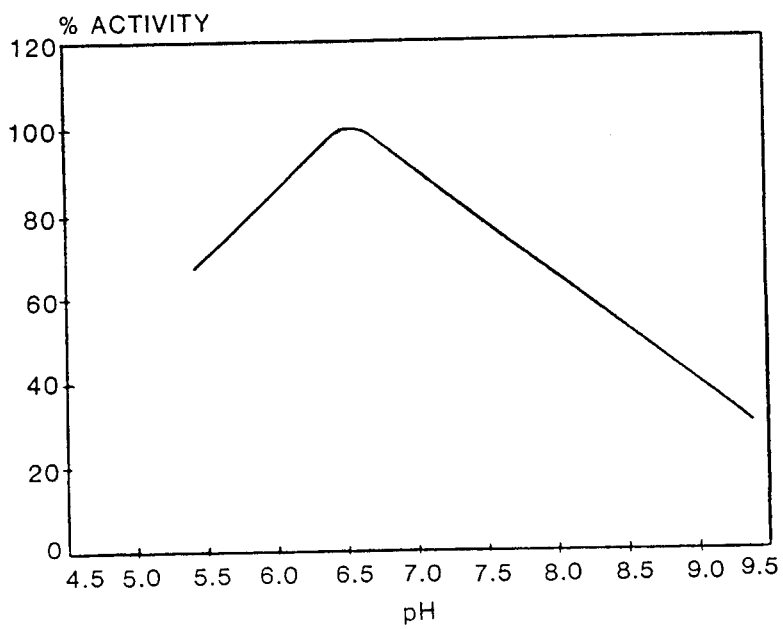

United States Patent [19]

Starnes et al.

[11] Patent Number: 4,632,905

[45] Date of Patent: Dec. 30, 1986

[54] MICROBIAL SULFHYDRYL OXIDASE

[75] Inventors: Robert L. Starnes, West Haven; Dennis M. Katkocin, Danbury; Carl A. Miller, Ridgefield; Robert J. Strobel, Jr., Norwalk, all of Conn.

[73] Assignee: Novo Laboratories, Inc., Wilton, Conn.

[21] Appl. No.: 738,764

[22] Filed: May 29, 1985

[51] Int. Cl.$^4$ ............................ C12N 9/02; C12R 1/66
[52] U.S. Cl. .................................... 435/189; 435/913; 426/42
[58] Field of Search .......................................... 435/189

[56] References Cited

U.S. PATENT DOCUMENTS 4,087,328 5/1978 Swaisgood ...................... 435/189 X

OTHER PUBLICATIONS

ATCC Catalogue of Strains I, 15th ed. 1982, p. 293.

Primary Examiner—Lionel M. Shapiro
Attorney, Agent, or Firm—Fidelman, Wolffe & Waldron

[57] ABSTRACT

A sulfhydryl oxidase from *Aspergillus sojae*, having a unit activity of about 2000 units per gm of protein enzyme preparation and essentially free from interfering activities.

8 Claims, 4 Drawing Figures

ACTIVITY OF SULFHYDRYL OXIDASE
AT DIFFERENT pH VALUES

ACTIVITY OF SULFHYDRYL OXIDASE
AT DIFFERENT TEMPERATURES

STABILITY OF SULFHYDRYL OXIDASE AT DIFFERENT TEMPERATURES

RESIDUAL SHs IN UHT MILK TREATED WITH ASPERGILLUS SOJAE SULFHYDRYL OXIDASE

THESE DATA ARE CORRECTED FOR THE AUTOOXIDATION RATE (SEE INSERT)

MICROBIAL SULFHYDRYL OXIDASE

This invention relates to microbial sulfhydryl oxidases, and in particular, to a sulfhydryl oxidase derived from *Aspergillus sojae*.

BACKGROUND OF THE INVENTION

Sulfhydryl oxidase (SOX) is an enzyme known to be present in several mammalian biological systems including bovine milk, human skin, and bovine kidney. As of the date hereof, the biochemical role of the enzyme is unknown.

The SOX recovered from bovine milk catalyzes the following reaction:

$$2R\text{—}SH + O_2 \rightarrow R\text{—}S\text{—}S\text{—}R + H_2O_2$$

with a specificity toward the tripeptide glutathione (δ-L-glutamyl-L-cysteinyl-glycine). Many proteins in their reductively denatured state have been reported as substrates for the SOX-catalyzed reaction. Bovine ribonuclease is one such protein. A rather broad specificity of the SOX enzyme toward small molecular weight mercaptans as well as to proteins has been found to exist.

SOX is of interest in applications where oxidation of free sulfhydryls to disulfide linkages is sought, particularly in place of the non-specific oxidants such as hydrogen peroxide, peracids, borates, bromates, etc. which have been employed heretofore to effect the disulfide bond formation. The non-specific oxidizing capability of these agents is disadvantageous; unwanted side reactions may occur. Enzyme-catalyzed reactions provide the selectivity desired, thereby avoiding side reactions.

One instance known to the art wherein treatment with sulfhydryl oxidase is of value is for the removal of a burnt flavor from Ultra-High Temperature (UHT) sterilized milk. For details of such usage of SOX, reference is made to U.S. Pat. Nos. 4,087,328 and 4,053,644.

The inventors hereof believe that the mammalian source SOX described in U.S. Pat. Nos. 4,087,328 and 4,053,644 never will be available in large quantities at economic prices, but a microbial source could provide a readily available, commercially attractive supply of SOX.

The object of this invention is to provide a microbially derived SOX.

RATIONALE OF THE INVENTION

A number of microbial species have been shown by the inventors hereof to elaborate a SOX activity. The source of the SOX preparations from these microorganisms was either microbially derived commercial enzyme preparations wherein SOX is a side activity or through specific fermentations of the microorganism for SOX. Some of the microbial species investigated by the inventors hereof for possible production of SOX activity; namely, *Aspergillus sojae*, *Aspergillus niger*, *Aspergillus oryzae*, *Bacillus subtilis*, and *Penicillium lilacinum*, were found to produce SOX activity at levels high enough for potential recovery of the SOX. Very low levels of SOX activity elaboration have been detected for *Bacillus licheniformis*, *Bacillus coagulans*, *Bacillus acidopullulyticus*, *Bacillus stearothermophilus*, *Mucor miehei*, and *Trichoderma reesei*.

It has, however, been possible to recover high unit activity SOX products through cultivation of *Aspergillus sojae*, and this invention specifically relates to SOX preparations from *Aspergillus sojae*.

BRIEF STATEMENT OF THE INVENTION

The present invention relates to the SOX elaborated by *Aspergillus sojae*, and preferably to SOX preparations essentially free of activities such as non-enzymatic oxidizing activity that interfere with the action of the SOX and free of enzymes, notably, proteinase, that affect the substrate adversely. The SOX enzyme catalyzes conversion of molecules possessing free sulfhydryl groups in the presence of oxygen to corresponding disulfides and hydrogen peroxide.

DISCUSSION OF THE INVENTION

SOX from microbial sources appears to be a constitutive enzyme, and, therefore, does not require induction. Its biochemical role in the microorganism is not known.

As already indicated, SOX is, in theory at least, available as a side activity in commercial enzyme preparations e.g., Fungamyl ®, Pectinex ®, and some amyloglucosidases. However, separation costs and yield loss in purification and/or concentration of the SOX would make the SOX product from such sources prohibitively expensive. Much the same can be said about recovery of SOX from cultivation of any microorganism source productive only of moderate levels of SOX activity. In addition, for treatment of milk, a SOX with high proteinase content would not be desirable, which factor might rule out some microbial species. *Bacillus subtilis* is known to be a proteinase producing microorganism.

A screen of industrially-relevant microorganisms has ascertained that *Aspergillus sojae* is a particularly good source of SOX. It has been found that the oxidase is elaborated both intracellularly and extracellularly in recoverable quantities when the microorganism is cultivated (aerobically in submerged fermentation). The cells are easily removed from the whole broth by conventional methods, e.g., centrifugation. Then the cell-free broth may be filtered using celite and finally concentrated by diafiltration (10,000 MW-cut-off), e.g., to about 200 U/ml, with an overall recovery of about 40%. Further, the enzyme has been found to be present in about equal quantities intracellularly. The SOX enzyme may easily be recovered from the cells in similar overall yields of about 40% by the above described recovery protocol following rupturing of the microbial cell. Cell rupturing can be achieved by high pressure disruption, sonication, enzymatic digestion or simply by cell autolysis, in general, the same methods heretofore employed to liberate and produce solutions of other intracellular fungal enzymes from various *Aspergillus* sp. Moreover, relatively low levels of acid and neutral proteinases are elaborated during cultivation of the *Aspergillus sojae*.

The reactions catalyzed by *Aspergillus sojae* SOX are the same or at least very similar to those catalyzed by bovine SOX, and involve, in both instances, conversion of two free sulfhydryl groups in the presence of molecular oxygen to the corresponding disulfide and generation of hydrogen peroxide.

SOX activity may be ascertained by two methods. The activity may be determined by measuring the oxygen consumed when a suitable substrate, e.g., reduced glutathione, is oxidized enzymatically to the corresponding disulfide. The stoichiometry involved is according to the equations 1 and 2 below, namely, ½ oxygen consumed per disulfide formed, when the reaction is carried out in the presence of catalase activity.

$$2RSH + O_2 \rightarrow RS-SR + H_2O_2 \qquad (1)$$

$$2H_2O_2 \rightarrow 2H_2O + O_2 \qquad (2)$$

The assay employs oxygen electrode techniques and is used with low MW compounds as substrates.

The SOX activity may be determined also by spectrophotometric techniques. Dithiobisnitrobenzoic acid (DTNB) specifically reacts with free sulfhydryls to yield a species which can be monitored spectrally at 412 nm. This assay is particularly useful in the enzymatic treatment of macromolecular compounds e.g., proteins.

The ability of low MW thiol-containing compounds to serve as substrates for SOX was determined polarographically at 30° C., pH 6.7. The microbial enzyme of this invention, like the bovine SOX enzyme, exhibits specificity toward the tripeptide glutathione. L-Cysteine, D-cysteine, L-cysteine ethyl ester, D,L-dithiothreitol, beta-mercaptoethanol, D,L-dithioerythreitol, and N-acetyl-L-cysteine are poor substrates for which enzyme activities range from 3-22% of the rate observed for glutathione (see Table I). Protein specificity was determined with proteins in their reductively denatured state. Reductive denaturation is accomplished by submitting the protein to a denaturant e.g., urea and a mercaptan such as beta-mercaptoethanol at pH 8.5. Renaturation is then achieved by incubating the reduced protein with the SOX for a period of time at pH 7.0. The progress of the renaturation can easily be assessed by reaction of the protein with DTNB. Both the microbial and the bovine enzyme renature reductively denatured proteins.

TABLE I

| Substrate Specificity of Sulfhydrl Oxidase | |
|---|---|
| Substrate | % of Activity with GSH |
| glutathione | 100 |
| dithioerythreitol | 6.6 |
| L—cysteine, ethyl ester | 21.8 |
| L—cysteine | 8.7 |
| D—cysteine | 4.1 |
| D,L—dithiothreitol | 5.6 |
| beta-mercaptoethanol | 4.2 |
| N—acetyl-L—cysteine | 3.0 |

The attached drawings to which reference is now made graphically illustrate various properties of the SOX enzyme.

Figure 2:
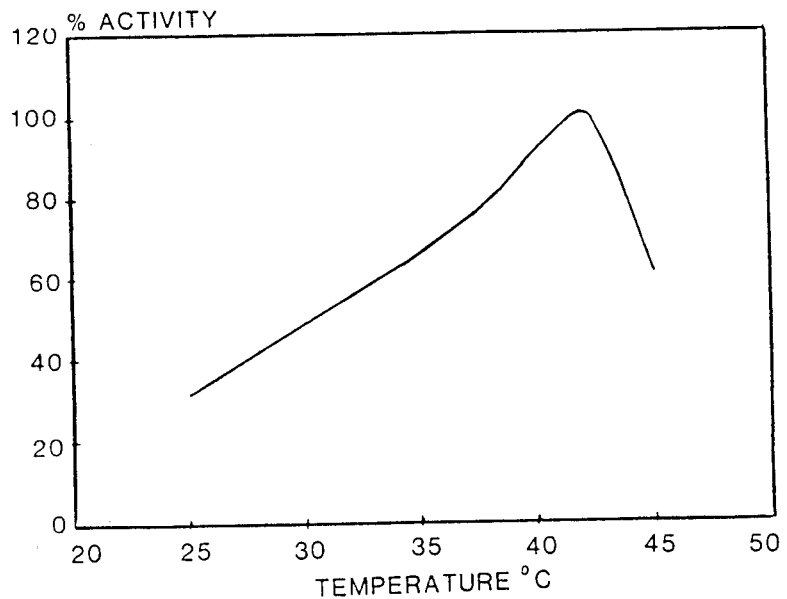
Figure 3:
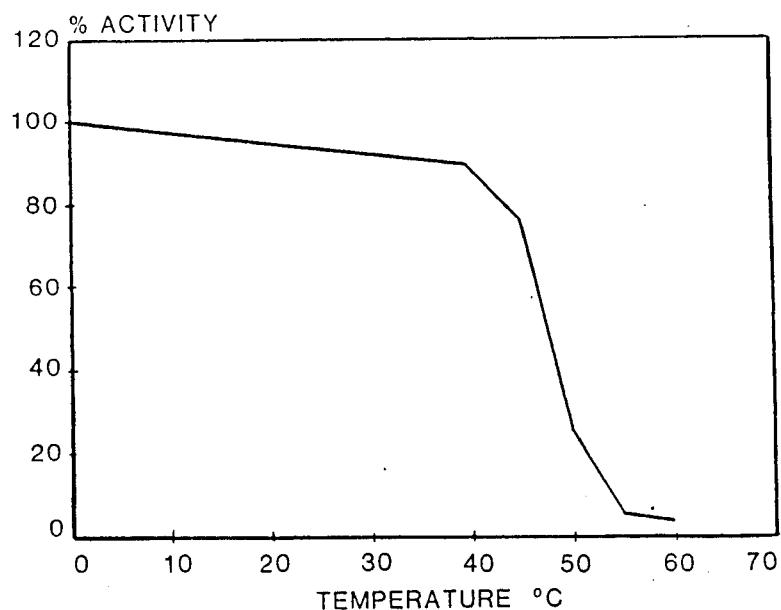
Figure 4:
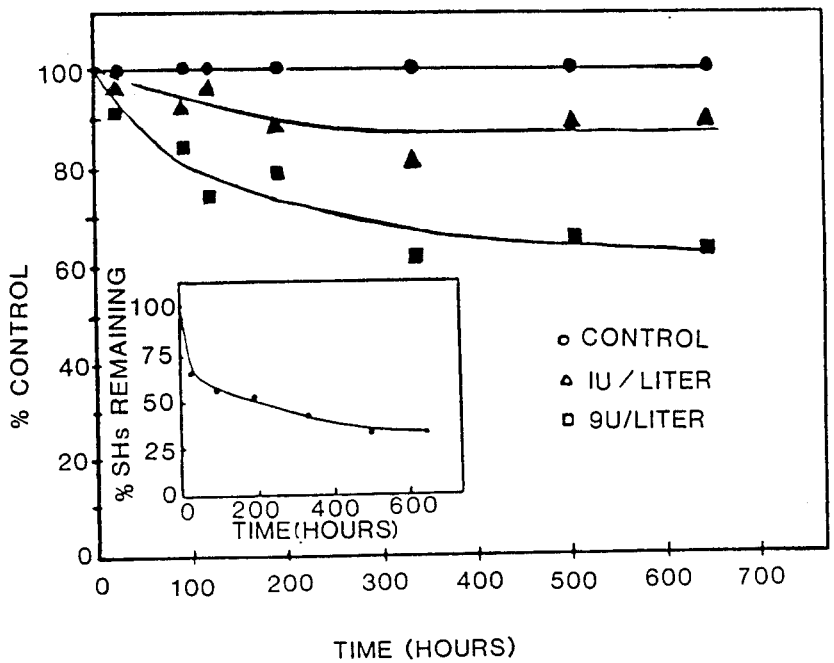

FIG. 1 shows activity at different pH levels;
FIG. 2 shows activity at different temperature levels;
FIG. 3 shows thermal stability; and
FIG. 4 shows the residual SH in UHT milk treated with the SOX.

Characterization of the SOX enzyme from *Aspergillus sojae* using glutathione as the substrate indicates activity over a broad range of pH (see FIG. 1). The pH optimum of the microbial SOX is 6.5; the bovine SOX has a pH optimum of 7.0. The temperature optimum of the microbial SOX is 42° C. (see FIG. 2), but the enzyme rapidly loses activity above 45° C. (see FIG. 3). The *Aspergillus sojae* SOX, unlike the bovine enzyme, is not inhibited by EDTA or $-CN$. For example, EDTA and $-CN$ at 1 mM concentrations inhibit bovine SOX almost completely. The microbial SOX of this invention is partially inhibited by $ZnSO_4$ at 1 mM concentration while this compound is non-inhibitory to bovine SOX.

As has been mentioned earlier, treatment with mammalian SOX is known to remove the burnt flavor from UHT milk. The *Aspergillus sojae* SOX can achieve the same reduction as the mammalian SOX. An evaluation was conducted in a commercial production facility where the UHT milk is produced from whole milk (3.5% fat content) by direct stream injection at 144° C. for nine seconds. The *Aspergillus sojae* SOX at doses of 1 U and 9 U per liter milk was introduced aseptically into the processed milk using a Tetra-Lacta Enzyme System (Tetra-Pak, Sweden). After one week storage at room temperature, the milk was organoleptically evaluated. The initial taste panel involving ten individuals overwhelmingly agreed that the SOX treated UHT milk was substantially more palatable i.e., negligible burnt flavor, compared to untreated UHT milk (see Table II below). This conclusion was corroborated by two independent taste panels, one of which was conducted at the production facility.

Not all SOX enzymes may be usable for this purpose. A semipurified preparation of the SOX recovered from a commercial alpha-amylase enzyme preparation Fungamyl ® was found to be unsuitable.

TABLE II

| Treatment of UHT Milk with Sulfhydryl Oxidase | |
|---|---|
| No Enzyme | Burnt-off flavor |
| 1 U SOX/liter | Less burnt |
| 9 U SOX/liter | Essentially no burnt taste |

It should be appreciated, however, that side activities present in the SOX may be detrimental for some uses of the SOX. Presence of proteinase, in particular, should be avoided when long term storage is being contemplated for SOX-treated UHT milk. In the test study described above, some of the SOX-treated UHT milk was stored for up to five months. Over this period of time, an off-flavor developed in the milk and coagulation of the milk occurred.

Investigations into the side activities present in an *Aspergillus sojae* SOX preparation, recovered by the protocol described above established the presence of two protease populations, one acid, one neutral. Semi-purified preparations of these proteases were recovered from the SOX to ascertain whether the proteases present in the SOX preparation were responsible for the off-flavor and coagulation. The proteases generated undesirable characteristics in milk treated therewith.

Size exclusion chromatography involving BioGel P100 (BioRad) will effectively reduce the content of these undesirable proteases by 80-90%.

In addition to size exclusion chromatography, protease activity can be removed by other well-known techniques such as ion exchange chromatography, bentonite treatment, or pH/temperature inactivation. Deproteinased SOX constitutes a preferred mode of this invention.

Another aspect of preferred modes of this invention resides in obtaining concentrated forms of the SOX. The *Aspergillus sojae* strains available to the inventors hereof elaborate 300-700 U/L in the broth. More concentrated forms are more desirable. Preferably, the SOX enzyme liquid preparation contains at least about 200 U/ml. The activity of the enzyme protein is about 2000 U per gram of enzyme protein preparation. The enzyme content in the fermentation broth and/or cell extract solutions may be concentrated readily by ultrafiltration to desired unit activity levels.

For further understanding of the invention, the following specific Examples thereof are provided.

The activity of the SOX preparation may be determined polarographically by measuring the oxygen consumed when a substrate e.g., reduced glutathione (GSH) is oxidized to the corresponding disulfide. The activity may also be determined spectrophotometrically using dithiobisnitrobenzoic acid (DTNB) which specifically reacts with a free sulfhydryl by measuring the absorption at 412 nm ($\epsilon = 13.6 \times 10^3 M^{-1} cm^{-1}$). Therefore, one unit of activity is defined as that amount of enzyme which catalyzes the consumption of 1.0 μmole of oxygen per minute or loss of 2.0 μmoles of free sulfhydryls per minute at 30° C., pH 6.7 using 1 mM GSH as substrate.

EXAMPLE 1

Cultivation of *Aspergillus sojae* for SOX production in submerged culture

SOX was produced by culturing the microorganism strain in liquid media that contained a metabolizable carbohydrate (e.g., cerelose) at concentration of 1 to 6%, an inorganic nitrogen source (e.g., $NaNO_3$ or $(NH_4)_2SO_4$), and salts of the essential minerals at the following suggested amounts per liter: $K_2HPO_4$, 2.0 g; $MgSO_4$, 0.3 g; $FeCl_3.6H_2O$, 27.0 mg; $ZnSO_4.7H_2O$, 7.25 mg; $MnCl_2.4H_2O$, 5.0 mg; $Na_2MoO_4.2H_2O$, 240 ug; $CuSO_4.5H_2O$, 125 ug; $H_3BO_3$, 30 ug. During growth, the pH was prevented from falling below 3.5 by addition of alkali (e.g., $KOH, NH_4OH$) or by use of a suitable buffer (e.g., citrate); the preferred pH was between 4.5 and 6.0. Oxygenation of the culture broth was such to assure rapid growth. The incubation temperature was maintained between 30° and 45° C., preferably between 35° to 40° C. The culture was harvested after suitable biomass had been produced, preferably before or at the time of carbohydrate depletion.

A comparison of three different strains of *Aspergillus sojae*, i.e., ATCC Nos. 20235, 20387 and 20388 demonstrated a variable capability from strain to strain in production of SOX under identical culture conditions. Strain 20387 produced nearly half as much SOX as strain 20235, while strain 20388 produced nearly twice as much SOX as strain 20235.

EXAMPLE 2

Recovery of *Aspergillus sojae* SOX

*Aspergillus sojae* ATCC 20235 was cultivated as described in Example 1. Then cells were removed from the whole broth by centrifugation and the cell-free broth was filtered using celite as filter aid. The broth was concentrated from 300 U/l to 200 U/ml using a Millipore Pellicon Cassette (10,000 MW-cut-off) followed by further concentration using Amicon diafiltration (10,000 MW-Cut-off). All procedures were conducted at pH 7.0, 4° C. The overall recovery was 40%.

The intracellular SOX was recovered from the cell mass is similar yields using the same centrifugation, etc. recovery protocol following release of the enzyme through mechanical disruption of the microbial cells.

EXAMPLE 3

Characterization of *Aspergillus sojae* SOX

The substrate specificity of SOX toward low MW compounds containing a free SH moiety was ascertained by polarographic methodology. The activities were measured relative to glutathione (GSH) at 30° C. in the following assay system: 1 mM test compound, 227 μM molecular oxygen, 50 mM potassium phosphate pH 6.7, and sufficient SOX to yield a linear decrease in oxygen during the first three minutes. The rates were corrected for auto-oxidation. The enzyme is highly specific toward GSH. L-Cysteine, D-cysteine, L-cysteine ethyl ester, D,L-dithiothreitol, beta-mercaptoethanol, D,L-dithioerythreitol, and N-acetyl-L-cysteine were oxidized at rates 3–22% of those observed for GSH. (The data has been provided in Table I.)

The pH and temperature optima presented in FIG. 1 were determined using GSH as the substrate at a concentration of 1.0 mM. The pH optimum measurements were made polarographically by the method described above at 30° C. in 0.2M boric acid, 0.05M citric acid, and 0.1M tertiary sodium phosphate in the proportions appropriate to achieve a desired pH from 5.0 to 9.0. The SOX exhibits activity over a broad pH range with an optimum at pH 6.5. Temperature optimum measurements were made polarographically in 0.1M sodium phosphate pH 6.7 between 25°–45° C. and are provided in FIG. 2. The SOX possesses a temperature optimum of 42° C. The stability of the SOX to temperature was measured by incubating the enzyme in 0.1M sodium phosphate pH 6.7 for one hour between 40°–60° C. The enzyme activity in the incubation was approximately 1 U/ml. The data are presented in FIG. 3. The SOX possesses relatively good temperature stability up to 40° C.

EXAMPLE 4

Removal of Burnt Flavor from UHT Milk

UHT milk was produced from whole milk (3.5% fat) by direct beam injection at 142° C. (for nine seconds) in a commercial production facility. The SOX from *Aspergillus sojae* (ATCC 20235) was diluted with 20 mM sodium phosphate pH 7.0 to levels of 220 U and 2000 U per liter and was then introduced into the UHT milk prior to packaging (0.5 l cartons) via the Tetra-Lacta Enzyme System (Tetra Pak, Sweden) at doses of 1 and 9 units per liter milk. The flow rate of the UHT milk during enzyme addition was 0.67 liter/minute. A total of 500 liters of milk was processed per dose level of the enzyme. A control without enzyme was also run.

The milk was stored for one week at room temperature and then submitted to organoleptic evaluation to determine if the burnt flavor had been affected relative to untreated milk. A taste panel comprised of ten individuals overwhelmingly appraised the enzyme treated milk as being more palatable than untreated milk. A dose dependent response was observed. A dose of 9 U/l almost completely removed the burnt flavor; burnt flavor was more noticeable in the 1 U/l case, but less so than that in the milk with no enzyme treatment. The results are provided in Table II.

EXAMPLE 5

Correlation of SH Level with Burnt Flavor

The residual SH level was determined according to procedures outlined in *Journal of Food Science* 45:317 (1980). In milk treated with the SOX according to the procedure of Example 4, a difference in SH levels relative to the reference milk was discernible by plotting the data according to the relationship $$[(SH)_t^{SOX}/(SH)_{t=0}^{SOX}]/[(SH)_{t=0}^{REF}]$$

versus time where (SH) is free sulfhydryl content, t is time of sample, $(SH)^{SOX}$ is enzyme treated milk and $(SH)^{REF}$ is untreated milk. The graph is shown in FIG. 4. The low SOX dosed milk exhibited a 10% reduction in —SH content, while the high SOX dosed milk had 40% reduction in measurable —SH. The data are corrected for the auto-oxidation rate observed in the control milk sample (see FIG. 4 insert). The slope of the auto-oxidation rate is substantial; the intial rate being 1.33 µM/hour followed by a much slower secondary rate ($6.25 \times 10^{-2}$ µM/hour).

EXAMPLE 6

Removal of Protease from *Aspergillus sojae* SOX

The *Aspergillus sojae* SOX preparation made according to Example 2 was profiled by BioRad P100 chromatography for neutral and acid proteolytic activity. Two preteases were identified: a neutral protease and an acid protease. A pool of the chromatographed SOX substantially reduced in both proteolytic activities was recovered. The protease containing fractions were recovered also.

Aseptic addition of the low protease SOX into cartons of UHT milk substantially reduced the rate of off-flavor formation. Essentially, the same test, this time using the protease fractions as additives, was carried out. A medicinal off-flavor, which resulted, was attributed to the acid protease, and a bitter off-flavor, which resulted, was ascribed to the neutral protease.

These results indicate that through gel filtration, greater than 80–90% reduction in protease content in the SOX can be achieved, and that the deproteinased SOX is superior for treatment of UHT milk.

We claim:

1. The sulfhydryl oxidase elaborated by *Aspergillus sojae* said sulfhydryl oxidase being characterized by a pH optimum of about pH 6.5 and a temperature optimum of about 42° C.

2. The deproteinased sulfhydryl oxidase elaborated by *Aspergillus sojae* said sulfhydryl oxidase being characterized by a pH optimum of about pH 6.5 and a temperature optimum of about 42° C.

3. An enzyme preparation comprising the deproteinased sulfhydryl oxidase elaborated by *Aspergillus sojae*, said enzyme having a unit activity of about 2000 U per gram of protein enzyme preparation said sulfhydryl oxidase being characterized by a pH optimum of about pH 6.5 and a temperature optimum of about 42° C.

4. An enzyme preparation comprising the deproteinased sulfhydryl oxidase elaborated by *Aspergillus sojae* in liquid form, said liquid preparation having at least about 200 U per ml of preparation said sulfhydryl oxidase being characterized by a pH optimum of about pH 6.5 and a temperature optimum of about 42° C.

5. A method for producing sulfhydryl oxidase which comprises cultivating a sulfhydryl oxidase producing strain of *Aspergillus sojae*, then recovering the enzyme from the culture broth.

6. A method for producing sulfhydryl oxidase which comprises cultivating a sulfhydryl oxidase producing strain of *Aspergillus sojae*, then releasing the enzyme from the microorganism cells, and thereafter, recovering the released sulfhydryl oxidase.

7. The process of claim 5 which further comprises deproteinasing the recovered sulfhydryl oxidase and concentrating the sulfhydryl oxidase to a liquid enzyme preparation containing more than about 200 U per ml of enzyme preparation.

8. The process of claim 6 which further comprises deproteinasing the recovered sulfhydryl oxidase and concentrating the sulfhydryl oxidase to a liquid enzyme preparation containing more than about 200 U per ml of enzyme preparation.

* * * * *